(12) United States Patent
Tran-Thi et al.

(10) Patent No.: US 9,977,000 B2
(45) Date of Patent: May 22, 2018

(54) MATERIAL FOR DETECTING PHENOL DERIVATIVES AND APPLICATIONS THEREOF

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE—CNRS, Paris (FR)

(72) Inventors: Thu-Hoa Tran-Thi, Montrouge (FR); Laurent Mugherli, Vaugrigneuse (FR); Ana Borta, Palaiseau (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days. days.

(21) Appl. No.: 14/994,655

(22) Filed: Jan. 13, 2016

(65) Prior Publication Data
US 2016/0202221 A1    Jul. 14, 2016

(30) Foreign Application Priority Data
Jan. 13, 2015   (FR) ..................... 15 50242

(51) Int. Cl.
*G01N 1/18* (2006.01)
*G01N 31/22* (2006.01)
(Continued)

(52) U.S. Cl.
CPC ............ *G01N 31/224* (2013.01); *G01N 1/30* (2013.01); *G01N 21/783* (2013.01); *G01N 31/22* (2013.01); *G01N 2001/302* (2013.01)

(58) Field of Classification Search
CPC .......... G02B 5/23; G01N 15/06; G01N 21/00; G01N 1/18
(Continued)

(56) References Cited

U.S. PATENT DOCUMENTS 6,638,885 B1 * 10/2003 McGrath ............... B01D 15/08
                                                        423/326
6,670,022 B1 * 12/2003 Wallace ............ H01L 21/02126
                                                        257/632
(Continued)

FOREIGN PATENT DOCUMENTS

CN       102590198 A    7/2012
CN        02362242 U    8/2012
(Continued)

OTHER PUBLICATIONS

Leventis et al.: "Durable Modification of Silica Aerogel Monoliths with Fluorescent 2,7-Diazapyreium Moieties. Sensing Oxygen near the Speed of Open-Air Diffusion", Chem. Mater. vol. 11, No. 10, 1999, pp. 2837-2845.
(Continued)

*Primary Examiner* — Brian J. Sines
(74) *Attorney, Agent, or Firm* — Young & Thompson

(57) ABSTRACT

Monolithic nanoporous material, which is self-standing (i.e. self-supported or cohesive), solid and transparent, essentially devoid of cracks, transparent to UV radiation, obtained by the Sol-Gel process, the material having a basic nature and including a reagent capable of generating a stained product by forming a bond with phenol, a basic compound or mixture of basic compounds and a compound or mixture of oxidant compounds, method for preparation and use in the detection and in the selective depollution of phenol or one of its derivatives.

10 Claims, 5 Drawing Sheets
(1 of 5 Drawing Sheet(s) Filed in Color)

(51) Int. Cl.
*G01N 1/30* (2006.01)
*G01N 21/78* (2006.01)

(58) Field of Classification Search
USPC .............. 422/68.1, 430; 436/178, 131, 173; 252/586
See application file for complete search history.

(56) References Cited

U.S. PATENT DOCUMENTS

| | | | |
|---|---|---|---|
| 2003/0138490 A1* | 7/2003 | Hu ....................... | A61K 9/0019 424/486 |
| 2005/0137315 A1* | 6/2005 | Aksay ..................... | C08K 3/36 524/492 |
| 2008/0220534 A1 | 9/2008 | Paolacci et al. | |
| 2009/0303660 A1* | 12/2009 | Nair ...................... | H01G 11/46 361/502 |
| 2012/0009687 A1* | 1/2012 | Acevedo .............. | G01N 31/221 436/113 |
| 2013/0130398 A1* | 5/2013 | Zang ...................... | G01N 21/78 436/128 |
| 2013/0280817 A1 | 10/2013 | Tran-Thi et al. | |
| 2016/0141616 A1* | 5/2016 | Seo ....................... | C01B 25/372 252/182.1 |
| 2017/0165946 A1* | 6/2017 | Poupa Parsigneau .......... | B32B 27/065 |

FOREIGN PATENT DOCUMENTS

FR 2 890 745 A1 3/2007
FR 2 969 295 A1 6/2012

OTHER PUBLICATIONS

F. Zhou et al.: "Determination of phenolic compounds in wastewater samples using a novel fiber by solid-phase microextraction coupled to gas chromatography" Analytica Chimica Acta 538 (2005) 63-70.

* cited by examiner

MATERIAL FOR DETECTING PHENOL DERIVATIVES AND APPLICATIONS THEREOF

FIELD OF THE INVENTION

The present invention relates to a material for detecting phenol and its derivatives and applications thereof.

BACKGROUND OF THE INVENTION

Phenol and its derivatives are highly toxic compounds. They are widely used in the production or manufacture of a large variety of aromatic compounds including explosives, fertilisers, lighting gases, paints, rubber, textiles, pharmaceutical products, perfumes and plastics, such as for example polycarbonates or epoxy resins. Phenol is routinely used as an intermediate in synthetic industrial chemical processes and notably in the petroleum, plastics, dye, leather, paper, soap industries. To a lesser degree, phenol and its derivatives are used in the composition of cosmetics and medicinal products. In some countries, phenol is also used as a mosquito repellent and as an insecticide and weed killer for agriculture. Consequently, phenol and its derivatives are found in the environment mostly via industrial emissions, but also via domestic activity (human and animal metabolism, waste water, household fuel oil combustion). Traces of phenol are also present in motor vehicle exhaust gases or tobacco smoke. Since 2006, the use of phenol as a disinfectant has been prohibited in France. However, phenol derivatives, such as chlorophenols for example, are frequently used as a substitute. As such, phenol and its derivatives are omnipresent, in air and in water, at variable concentrations according to human activity.

Phenol is toxic by inhalation, in contact with skin and if swallowed. It is also liable to induce genetic abnormalities. In the event of contact, it causes skin burns and eye lesions. Repeated or prolonged exposure may induce severe effects for organs, such as: digestive disorders, headaches, salivation, anorexia, vomiting and loss of appetite. It also causes bone marrow damage.

The restrictive occupational exposure limits for air in work premises have been set in France and in the European Union to 2 ppm (7.8 mg/m$^3$) for a weighted average over 8 hours and to 4 ppm (15.6 mg/m$^3$) for short-term exposure of not more than 15 min (as per the toxicology file of the French National Institute for Research and Health-INRS).

At the present time, sensitive, selective and reliable detection of phenol in a gas mixture is performed using an indirect method with gas sampling and subsequent analysis in a laboratory.

In order to detect phenol in solution, it is necessary to use a different method, the reference being the colorimetric method based on 4-aminoantipyrine (AAP), wherein phenol cannot be added last, and the reagents, previously stored separately, must be added at the last minute, which renders the method very complex. Finally, these methods can only be used for detection, and under no circumstances for depollution, if the presence of phenol is established.

There are numerous methods for detecting phenol in aqueous solution or in the air.

The detection methods are essentially broken down into three categories: chromatographic methods, electrochemical methods and colorimetric methods. Further methods also exist and are under development such as for example methods based on mass microvariation (piezoelectric resonators).

Chromatographic methods require costly apparatuses and complex procedures. In addition, they induce a response time when they are used indirectly (field sampling following laboratory analysis).

Electrochemical methods are not readily adaptable for detection in air and frequently require the addition of modified electrodes containing nanoparticles, polymers or enzymes. The costs of such electrodes and the ageing thereof under actual conditions of use may constitute an impediment to the industrialisation thereof.

Chromatographic and electrochemical methods exhibit intrinsic complexity either in the raw material (enzymes, nanoparticles, etc.), in the preparation (materials), in the operating protocol thereof (sampling, extraction, concentration, purification, addition of other reagents, assay), or in the measurement per se (complex, bulky apparatuses). With this complexity, a relatively high cost and a potentially long time to obtain results are thus associated. Furthermore, a certain expertise is required to run the samples and interpret the results, as these methods are far from being simple to use.

Colorimetric methods have the advantage of being simpler to use in terms of preparation, sampling, measurement, and obtaining results. These methods are generally direct (no retrospective laboratory analysis). The response is thus quicker. Furthermore, the apparatus required is inexpensive, and more compact.

In the literature, there are a large number of colorimetric methods for detecting phenol or its derivatives in solution, using reagents in an acid medium, such as p-diazobenzenesulphonic acid (DABS) which gives rise to a yellow colour, the mixture Fe(II)/1,10-phenanthroline which produces pink staining, the mixture formaldehyde-sulphuric acid (FSA) and the purple staining thereof, or iodine bromide which forms an absorbent product in the UV range. Reactions in basic medium have also been described, using for example Folin-Ciocalteu's reagent, which develops blue staining. Further reagents require extraction with an organic solvent of the stained product, such as for example the brown product of Millon's reagent, the pink product of MBTH (3-Methyl-2-benzothiazolinone hydrazone hydrochloride monohydrate) in the presence of an oxidant, or the blue load transfer complexes derived from 2,3-dichloro-5,6-dicyano-p-benzoquinone (DDQ). Some of these reagents are costly, others toxic. Furthermore, they may require an extraction step before the colour analysis. They are not all sufficiently sensitive and selective.

The most commonly used method which provides satisfactory sensitivity and selectivity, probably because it is the simplest, is based on the use of 4-aminoantipyrine (AAP). Moreover, it is the reference method cited by the French National Institute for the Industrial Environment and Risks (INERIS). The method involves the formation of a quinoid complex between 4-aminoantipyrine and phenol in a basic medium (preferentially pH=9 or 10) and in the presence of the oxidant potassium hexacyanoferrate. Staining develops after 5 min for concentrations greater than 1 mg/l i.e. approximately 10 µM (193 ppb) and the quinoid compound has an absorption peak around 510 nm. It should be noted that for concentrations below 1 mg/l, INERIS recommends three successive extractions with chloroform, which renders the operation notably more complex. In the literature, this reaction is described with various AAP compounds and various oxidants, and with various [AAP]:[oxidant] ratios, for example Analytical Chimica Acta, 467, 2002, 105-114, Jour. Chem. Soc. Pak., 27, 2005, 271-274, or Jour. Organ. Chem., 8, 1943, 417-428.

The AAP compounds mentioned in some publications are of interest, notably those making it possible to increase sensitivity by means of a higher molar extinction coefficient. However, they are not easy to acquire as they are mostly synthesised on commission. The majority of methods based on AAP described in the literature enable selective and sensitive detection of the order of a few ppb, but they all use a chloroform extraction step which complicates the protocol and prolongs the duration thereof. If seeking to do away with this extraction step, the INRS guidelines and rare publications with direct detection in aqueous solution indicate a significant drop in sensitivity: the method only works correctly for concentrations greater than 200 ppb (1 mg/l, 10 µM). All these methods use excess oxidant, and the order of use of the reagents is always the same, i.e.: 1) buffer solution, 2) phenol, 3) AAP, 4) oxidant. The waiting time before measuring the absorbance varies from 5 to 30 min.

Attempts to adapt this reference phase in liquid phase to the detection of phenol in gas phase are not convincing. Indeed, only two patents have been filed, and adaptation required a significant complication of the method [Patent documents CN102590198 and CN202362242U]. A plurality of steps are added, notably dissolution in acid medium, distillation, stripping, heating, extraction. Furthermore, in one of the patents, the reagents are added sequentially, which complicates the method further [Patent document CN202362242U].

The disclosure above demonstrates that, at the present time, there is no simple and direct colorimetric method based on the use of AAP or its derivatives, which is selective and sensitive, and which enables the detection of phenol in solution by adding same last. In other words, there is no method where the addition of the sample constitutes the final step.

The methods developed for the detection of phenol in air are much less numerous. By an overwhelming majority, known methods are performed in a plurality of steps. Firstly, sampling of air containing phenol is performed via a tube filled with silica gel or resin (typically XAD7), and this sampling is then followed by desorption with solvents and derivatisation with a silylation agent, then, an assay is performed, by gas chromatography with flame ionisation detection or by liquid chromatography with UV or electrochemical detection.

The only direct method, i.e. with no retrospective laboratory analysis, consists of using GASTEC (No. 60) or DRAEGER (Phenol 1/b, MSA Phenol-1) graduated tubes. The detection principle is based on reacting phenol in an acid medium with $(NH_4)_2Ce(NO_3)_6$ (for GASTEC) and $Ce(SO_4)_2$ (for DRAEGER), which produces a change of colour from yellow to brown-green. The stained product spreads through the tube with a rate dependent on the phenol concentration for a gas stream pumped at a flow rate defined by the manufacturer. The concentration reading is performed using the graduations printed on the tube. The most effective is the GASTEC tube, with a detection range of 0.4 to 187 ppm with an error of 10% to 15% indicated by the manufacturer. The advantage of this detection is the simplicity thereof, but the detection reaction is not selective, and it is necessary to apply a correction factor based on the humidity and the temperature. As such, these tubes do not provide the selectivity or the precision required for comparison with an occupational exposure limit value as per INRS. These tubes cannot be used in water, which represents a further limitation with the method.

Therefore, at the present time, there is no direct, selective and sensitive colorimetric method suitable for detecting phenol in gas phase. Furthermore, no universal method for the detection both in a gas mixture such as air or in a solution, for example aqueous, by merely contacting a functional material with the fluid, has been developed to date.

It would thus be desirable to have such a method. The method should enable direct, optical or visual detection feasible in the field with portable equipment, to prevent the transport of samples to be tested to a laboratory equipped to make such a measurement. The method should also be simple. It should be suitable for use equally well for the detection of phenol or a phenol derivative in a gaseous or liquid mixture. The method should be suitable if possible not only for use for detection, but also for selective depollution of phenol and its derivatives.

SUMMARY OF THE INVENTION

The present invention makes it possible to solve all or some of the technical problems associated with the detection of phenol or a phenol derivative mentioned above.

After long research, the inventors have developed a method inspired by the colorimetric reaction in solution based on AAP, but with major changes, which have resulted in a precise and reliable, but considerably simplified, method, by conceiving a novel material.

With the reference method, the oxidant is always used in excess and the order of addition of the reagents is very important: 1) buffer solution, 2) phenol, 3) AAP, 4) oxidant. In the presence of excess oxidant, if this order is not observed, the change of colour does not occur.

However, the material according to the present invention already contains all the reagents required for the stained reaction. Therefore, the phenol (or phenol derivative) is necessarily contacted with the other reagents last. The preservation of the stained reagents within the material according to the present invention was not obvious in the presence of oxidant, particularly as all the methods described in the literature use excess oxidant (typically 6 molar equivalents).

Moreover, transparent monolithic nanoporous materials obtained using the Sol-Gel process have previously been described in FR2890745 and FR2969295. However, the materials described in these patent documents do not have a basic nature, which is necessary for the proper completion of the reaction in the present invention. Furthermore, the incorporation in the same sol gel matrix of a colorimetric reagent and an oxidant had never previously been described or suggested.

For this reason, the present application relates to a monolithic nanoporous material, which is self-standing (i.e. self-supported or cohesive), solid and transparent, essentially devoid of cracks, transparent to UV radiation, obtained by the Sol-Gel process, said material having a basic nature and comprising a reagent capable of generating a stained product by forming a bond with phenol or a phenol derivative, a basic compound or mixture of basic compounds and a compound or mixture of oxidant compounds.

By way of reminder, a Sol-Gel material is a material obtained by a Sol-Gel method. This method may notably be implemented using as precursors alkoxides having the formula $M(OR)_n$, $R'-M(OR)_{n-1}$ or sodium silicates. M is a metal, notably silicon, and R or R' alkyl groups, n is the degree of oxidation of the metal. In the presence of water, the hydrolysis of the alkoxy groups (OR) occurs, forming small particles generally less than 1 nanometer in size. These particles aggregate and form clusters which remain suspended without precipitating, and form a sol. The increase in the clusters increases the viscosity of the medium which gels. A Sol-Gel material is obtained by drying the gel, removing the solvent from the polymer lattice formed. This material absorbs in UV but not in the visible range.

In the present application and hereinafter, the expression "essentially devoid of cracks" means that the monolithic material is devoid of cracks liable to interfere with the optical measurement.

The Sol-Gel material according to the invention may be prepared essentially using one or a plurality of first polyalkoxysilane(s) chosen among the following compounds: (chloromethyl)triethoxysilane; 1,3-dimethyltetramethoxydisiloxane; ethyltrimethoxysilane; triethoxy(ethyl)silane; triethoxymethylsilane; triethoxy(vinyl)silane; trimethoxymethylsilane; trimethoxy(vinyl)silane; tetraethoxysilane or tetramethoxysilane and advantageously a single polyalkoxysilane and more particularly tetramethoxysilane (TMOS) and units of one or a plurality of second polyalkoxysilane(s) chosen among the following compounds: (N-(3-(trimethoxysilyl)propyl)ethylenediamine; 3-aminopropyltriethoxysilane (APTES) and 3-aminopropyltrimethoxysilane and advantageously 3-aminopropyltriethoxysilane, in a molar ratio of first polyalkoxysilane(s)/second polyalkoxysilane(s) of 1:0.01 to 1:1, preferably 1:0.01 to 1:0.50, notably 1:0.01 to 1:0.30, particularly 1:0.01 to 1:0.15, more particularly 1:0.02 to 1:0.06; preferably the first polyalkoxysilane is TMOS. It should be noted that (N-(3-(trimethoxysilyl)propyl)ethylenediamine, 3-aminopropyltriethoxysilane (APTES) and 3-aminopropyltrimethoxysilane comprise at least one primary amine function.

Porous Sol-Gel materials suitable for being prepared essentially using one or a plurality of first polyalkoxysilane(s) and a single second polyalkoxysilane, and particularly a single first polyalkoxysilane and a single second polyalkoxysilane, are preferred. Of the second polyalkoxysilanes used in the composition of the material, 3-aminopropyltriethoxysilane (APTES) are preferred.

Particularly preferred Sol-Gel materials are prepared essentially from tetramethoxysilane (TMOS) and 3-aminopropyltriethoxysilane (APTES) in a molar ratio of TMOS: APTES of 1:0.01 to 1:0.30, preferably 1:0.01 to 1:0.15, advantageously 1:0.01 to 1:0.10, notably 1:0.02 to 1:0.06, more particularly 1:0.03 and thus comprise units of one and the other in such proportions.

The reagent molecule used is a reagent capable of generating a stained product by forming a bond with phenol or a phenol derivative. More specifically, the reagent is a compound enabling a colour to be developed by forming a generally covalent bond with phenol or phenol derivative, to form a coloured product, for example a quinoid compound. The reagent molecule is preferably AAP but may also be an AAP compound, such as for example a compound corresponding to formula I

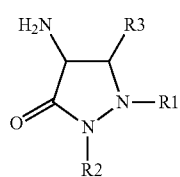

formula I where: R1 is an alkyl radical containing 1 to 30, notably 1 to 12, preferentially 1 to 6 carbon atoms, linear or branched, or an aryl radical, preferably phenyl, preferentially a radical $C_6H_5$, $CH_3$ or $C_2H_5$; R2 is a phenyl or para-aminophenyl radical, preferentially the latter; R3 is an alkyl radical containing 1 to 30, notably 1 to 12, preferentially 1 to 6 carbon atoms, linear or branched, or optionally substituted phenyl, preferably in the para position, for example by an amino or halogen radical, such as a para-aminophenyl or parachlorophenyl radical.

A monolithic nanoporous material according to the invention also contains a basic compound or mixture of basic compounds. Indeed, the method for preparing monolithic nanoporous material according to the invention requires a basic medium, i.e. corresponding to a pH in the sol greater than 7, and preferentially of 9 to 10. One of the methods for obtaining this basic medium is the use of a buffer solution, such as for example a phosphate, 2-amino-2-(hydroxymethyl)-1,3-propanediol, carbonate, glycine-sodium hydroxide buffer, or preferentially a borate buffer, to obtain a pH equal to preferably approximately 9 or 10. Optionally, sodium hydroxide may also be used, alone or in a mixture with the above-mentioned buffer solutions. The monolithic nanoporous material according to the invention thus contains such basic compounds or mixture of basic compounds with the corresponding weak acid if applicable. For example using borate buffer at pH 10, the monolithic nanoporous material according to the invention contains borate ions, boric acid (weak acid essentially in non-dissociated form in dilute solution) and sodium hydroxide. This basic property is necessary for the proper completion of the reaction which makes it possible to incorporate in the same matrix a stained reagent and an oxidant.

A monolithic nanoporous material according to the invention also contains a compound or mixture of oxidant compounds. The oxidant compound or oxidant compounds are advantageously chosen in the group consisting of potassium persulphate, potassium peroxomonosulphate; hydrogen peroxide or potassium hexacyanoferrate. The latter is advantageously used which enables a good compromise between smoothness of the oxidation and reaction rate. Oxidants other than those in the non-exhaustive list above are possible.

The oxidant compound or oxidant compounds are particularly chosen in the group consisting of potassium hexacyanoferrate, potassium persulphate, potassium peroxomonosulphate; hydrogen peroxide or a mixture of potassium hexacyanoferrate and one or a plurality of further oxidant compounds.

The monolithic nanoporous material according to the invention is self-standing. In other words, it is self-supported or cohesive. By way of reminder, a material is described as cohesive, as opposed to friable (e.g. snow) or liquid (gel), to denote the ability thereof to remain stable under the action of internal forces.

Note that in the present application, conventionally the indefinite article "a" should be considered as a generic plural (meaning "at least one" or "one or a plurality"), unless demonstrated otherwise by the context (1 or "a single"). As such, for example, when it is said above that the monolithic nanoporous material according to the invention comprises a reagent capable of generating a stained product by forming a bond with phenol or phenol derivative and comprises a basic compound, it should be understood that the material contains one or a plurality of such reagents or basic compounds.

Under preferential conditions of use of the invention, the reagent capable of generating a stained product by forming a bond with phenol or a phenol derivative is AAP, and the basic compound or mixture of basic compounds is chosen from among borate ions and sodium hydroxide, the oxidant compound or oxidant compounds is potassium hexacyanoferrate or a mixture of potassium hexacyanoferrate and one or a plurality of further oxidant compounds.

A monolithic nanoporous material according to the invention contains a quantity of reagent capable of generating a stained product by forming a bond with phenol or phenol derivative in relation with the use of said material. For use for depollution, large proportions of reagent capable of generating a stained product by forming a bond with phenol or a phenol derivative will advantageously be used. However, large proportions would be redhibitory in use for detection, for example due to saturation of a detector.

The ratio by weight of [reagent capable of generating a stained product by forming a bond with phenol]:[compound or mixture of oxidant compounds] may also be dependent on the envisaged use.

For example, by weight, in the context of detection, a ratio by weight will advantageously be used:
  of 25% to 0.005%, preferably 18% to 0.008%, notably 5% to 0.008%, particularly 2% to 0.1%, more particularly 1% to 0.1% of molecular probe.
  of 5% to 0.05%, preferably 3% to 0.1%, notably 2% to 0.2%, particularly 1% to 0.4%, more particularly 0.7% to 0.5% of basic compound or mixture of basic compounds.
  of 15% to 0.01%, preferably 10% to 0.02%, notably 8% to 0.02%, particularly 2% to 0.05%, more particularly 1% to 0.1% of compound or mixture of oxidant compounds.

And by weight, in the context of depollution, a ratio by weight will advantageously be used:
  of 50% to 0.05%, preferably 30% to 0.03%, notably 18% to 0.05%, particularly 5% to 0.1%, more particularly 1% to 0.1% of probe molecule.
  of 5% to 0.05%, preferably 3% to 0.1%, notably 2% to 0.2%, particularly 1% to 0.4%, more particularly 0.7% to 0.5% of basic compound or mixture of basic compounds.
  of 25% to 0.01%, preferably 12% to 0.02%, notably 8% to 0.02%, particularly 2% to 0.05%, more particularly 1% to 0.1% of compound or mixture of oxidant compounds.

Those skilled in the art will adapt these different values by weight such that the ratio by weight of [probe molecule]:[compound or mixture of oxidant compounds] in the context of detection is for example 10:1 to 1:3, preferably 5:1 to 1:2, particularly 1:1. For a high weight ratio, a certain instability may be encountered, instability meaning an intensification of the materials colour before exposition. For a very low weight ratio, it is possible to obtain slower kinetics, slow kinetics meaning that the response of the sensor may take up to several weeks.

Similarly, those skilled in the art will adapt these different values by weight such that the ratio by weight of [probe molecule]:[compound or mixture of oxidant compounds] in the context of depollution is for example 15:1 to 1:3, preferably 5:1 to 1:2, particularly 1:1.

When seeking to produce a monolithic nanoporous material according to the invention intended for depollution, large quantities of reagent capable of generating a stained product by forming a bond with phenol or phenol derivative and small quantities of oxidant are advantageously used.

The present application also relates to a method for preparing a monolithic nanoporous material above, characterised in that, in the same container, one or a plurality of sol-gel precursors is added to a solution of reagent capable of generating a stained product by forming a bond with phenol or phenol derivative, followed by adding the oxidant compound or mixture of oxidant compounds followed by the basic compound or mixture of basic compounds to obtain a pH greater than 7, where at least one of these compounds is in aqueous solution, to obtain a sol which is placed in one or a plurality of moulds, preferably the moulds are sealed hermetically, and the solvents are evaporated in an inert atmosphere to obtain the monolithic nanoporous material sought.

Under preferential conditions of use of the method above,
  the reagent capable of generating a stained product by forming a bond with phenol or a phenol derivative is in solution in an alcoholic solvent, preferably methanol.
  the basic compound or mixture of basic compounds is added in sufficient quantity to give the reaction medium a pH greater than 7, preferably 7.5 to 10.5, notably 8 to 10, particularly of 8.5 to 9.5, more particularly approximately of 9.
  the moulds are sealed hermetically to enable gelling without solvent evaporation. Maintenance under such conditions lasts for example 0 to 192 hours, preferably 4 to 120 hours, notably 12 to 96 hours, particularly 24 to 72 hours, more particularly approximately 48 hours.
  Evaporation of the solvents is carried out in an inert atmosphere, for example with as a carrier gas argon, nitrogen or air, and preferably in a nitrogen atmosphere. The evaporation of the solvents is advantageously carried out slowly, for example for 4 weeks. Preferentially, the carrier gas used for drying has a relative humidity suitable for preventing cracking of the material.

If, under preferential conditions of use of the invention, the basic compound or mixture of basic compounds is added to the reaction medium after the sol-gel precursors, it is possible, although less convenient, to change the order of introduction.

Incorporating in a single material a reagent capable of generating a stained product by forming a bond with phenol or phenol derivative, and an oxidant compound or mixture of oxidant compounds, essential components for the reaction in the same material as that containing the reagent capable of generating a stained product by forming a bond with phenol or a phenol derivative was a challenge. Indeed, the material needed to remain transparent, monolithic, and exhibit a change of optical properties related to the concentration of phenol or phenol derivative.

The monolithic nanoporous materials according to the present invention have very interesting properties. They consist of a nanoporous matrix permeable to gases and liquids incorporating all the reagents required for detecting the phenol or phenol derivative. The reaction of this matrix with phenol is easily detectable by a change of optical properties (colour/absorbance/reflectance). The formulation of the material according to the invention enables same to be directly exposed to phenol or phenol derivative in gas phase but also in liquid phase, with great simplicity of use, while allowing direct optical detection.

A material according to the invention is stable for several months.

These Sol-Gel matrices may thus be used to detect phenol, or a phenol derivative, such as for example alkoxyphenols, nitrophenols, chlorophenols, or polyaromatic phenols. This detection may be carried out equally well in a gas mixture or in liquid phase, in aqueous solutions, or in some solvents or mixtures of solvents and water. The function thereof is based on a chemical reaction taking place in the matrix which generates an optically detectable signal. Tracking this optical signal over time makes it possible to determine the reaction rate, which is then correlated with the concentration of gaseous compound under test for example by means of a calibration curve. The optical detection is rapid and feasible in situ in a single step.

The monolithic nanoporous materials according to the present invention are suitable for detecting concentrations of phenol or phenol derivative from 15 ppb, or concentrations well below the current limit of 193 ppb for the reference reaction with AAP, as recommended by INERTS in France. The few ppm mentioned by INRS for exposures of workers are all the more detectable with the monolithic nanoporous materials according to the present invention.

The monolithic nanoporous materials according to the present invention make it possible to solve with simplicity a plurality of technical problems associated with the detection of phenol or phenol derivative. They enable direct detection (optical or visual measurement), suitable for being performed in the field with portable equipment.

It is sufficient to place a monolithic nanoporous material according to the present invention, ready for use and incorporating one or a plurality of probe molecules in contact with a fluid containing phenol or phenol derivative to initiate a chemical reaction which generates a change of the optical properties of the matrix, a change which is directly correlated with the concentration of phenol or phenol derivative in the fluid.

The monolithic nanoporous materials according to the present invention enable the detection or phenol or phenol derivatives in a gas or liquid mixture.

Finally, technical problems purely associated with the use of porous materials have also been resolved: an oxidant is incorporated in a formulation stable for several months. A basic buffer solution is also incorporated in the same formulation. It was not obvious that incorporating an oxidant or a basic buffer solution among the colorimetric reagents, in a porous material, could be done while retaining the qualities thereof, notably the transparency, mechanical strength and detection function. Finally, these porous materials can not only be used for detection, but also for selective depollution of phenol and its derivatives.

The phenol compounds are for example alkoxyphenols, nitrophenols, chlorophenols, or polyaromatic phenols. Particular mention may be made of 4-methoxyphenol, 2-nitrophenol, 2,4-dichlorophenol, or naphthol, but also cresol, catechol, resorcinol, 2,4-dimethylphenol, 4-chloro-3-methylphenol, 4-nitrophenol, 2,4-dinitrophenol, 4,6-dinitrophenol, 4-chlorophenol, 2-chlorophenol, 2,4,6-trichlorophenol, pentachlorophenol.

In sum, the novel nanoporous monolithic materials according to the invention make it possible to carry out direct colorimetric detection. The use thereof for detecting phenol or phenol compounds, regardless of the origin thereof, offers the advantages of simplicity of use, selectivity for phenols, and low production cost. They can be used equally well in a gas mixture, in aqueous solutions, or in some solvents or mixtures of solvents and water.

These properties are illustrated hereinafter in the experimental section. They justify the use of the nanoporous monolithic materials according to the invention described above, in the detection, measurement, but also in the selective depollution of phenol and its derivatives.

The invention proves to be useful notably within the scope of daily or weekly monitoring at the workplace, or to detect pollution peaks in air or in water, in particularly in residual water.

With a view to the use thereof, the materials according to the invention may notably be used as follows:

For detection in gas phase, a user merely needs to place a material according to the invention in contact with the phenol or phenol compounds to be detected in a gas mixture, such as for example air. This contact may be performed by placing the matrix in an atmosphere wherein it is sought to monitor the content of gas to be detected (static measurement), or by passing a gas stream over the matrix (dynamic measurement).

The flow rate range for the gas stream may be for example between 20 mL/min and 1 L/min, preferentially between 200 and 500 mL/min. An excessive gas flow rate would involve stream loss. The reaction product between the various reagent compounds of the matrix and the gaseous compounds sought absorbs in the visible range, with a peak close to 510 nm for AAP. With the absorbance is associated a change of colour of the matrix visible to the naked eye. The detection may thus be qualitative or quantitative, and may cover phenol or phenol derivative concentrations between around ten ppb and several ppm. During exposures, a material according to the invention remains transparent and no crack detectable with the naked eye appears.

For this reason, the present application also relates to the use of the monolithic nanoporous materials described above in the detection of phenol or one of its derivatives for example 4-methoxyphenol, 2-nitrophenol, 2,4-dichlorophenol, or naphthol, but also cresol, catechol, resorcinol, 2,4-dimethylphenol, 4-chloro-3-methylphenol, 4-nitrophenol, 2,4-dinitrophenol, 4,6-dinitrophenol, 4-chlorophenol, 2-chlorophenol, 2,4,6-trichlorophenol, pentachlorophenol.

The present application particularly relates to a method for the detection of phenol or its derivatives for example 4-methoxyphenol, 2-nitrophenol, 2,4-dichlorophenol, or naphthol, but also cresol, catechol, resorcinol, 2,4-dimethylphenol, 4-chloro-3-methylphenol, 4-nitrophenol, 2,4-dinitrophenol, 4,6-dinitrophenol, 4-chlorophenol, 2-chlorophenol, 2,4,6-trichlorophenol, pentachlorophenol, comprising the steps consisting of providing a nanoporous material according to the invention contacting with a fluid optionally containing phenol or one of its derivatives, detecting any change of optical properties of the reagent capable of generating a stained product by forming a bond with phenol or a phenol derivative.

Under preferential conditions of use, the method described above further comprises a step consisting of measuring the change of optical properties, which enables a quantitative measurement of phenol and its derivatives.

For detection in solution, the user may merely place a nanoporous material according to the invention in contact with the sample to be measured. This contact may be performed by merely steeping (static measurement), or by circulating a solution over a nanoporous material according to the invention with a certain flow rate, preferably known (dynamic measurement). During this contact, a progression of the absorbance over time is observed, in the 400-800 nm range, with a peak close to 510 nm for AAP and phenol, which can be tracked. With this progression of absorbance is associated a change of colour visible to the naked eye. This is an important advantage as it makes it possible to make qualitative or quantitative measurements on the nanoporous material according to the invention.

After having contacted the nanoporous material according to the invention with the solution, it is also possible to make the measurement directly on the solution, as it changes colour also, the stained product being in solution. The nanoporous material according to the invention then acts as a container containing all the reagents required for the stained reaction, which makes it possible to avoid steps of storing, preparing and adding reagents (weighing, buffer solutions, dilutions, etc.), which already enables a significant simplification with respect to the reaction in solution according to the prior art.

The reaction also has the advantage of also taking place if certain polar solvents are mixed with water, such as cyclic alcohols or ethers, in particular ethanol or tetrahydrofuran.

The present application also relates to the use of a monolithic nanoporous material described above in the selective depollution of phenol or one of its derivatives, notably in air or other gas mixtures. In particular, these materials may be used for purifying the atmosphere in closed spaces, optionally confined or having a system for recycling air or a gas mixture.

Depollution may be carried out according to the same protocols as indicated above for detection.

The main advantages in relation to current depollution methods are not only selectivity, but also the change of colour which makes it possible to determine the state of wear of the material in real time. By means of the absorbance measured in a monolithic material, it is possible to estimate the trapping yield. In 500 mL/min, approximately 5% in moles of the phenol circulating in the flow is trapped with a single monolithic material such as that prepared hereinafter in example 1. Under optimal conditions in respect of flow, shape and number of monoliths, this trapping yield may be increased significantly.

Depollution may also be carried out in water, but in this case it is necessary to adapt the formulation to prevent the release of the reaction products into the solution.

In general, for depollution, greater quantities of nanoporous material according to the invention are used. Likewise, blocks of nanoporous materials according to the invention are then used to increase the specific area thereof, promote exchanges and thus speed up the time required for depollution.

The preferential conditions of use of the monolithic nanoporous materials described above also apply to the other subject matter of the invention mentioned above, notably to the methods for the preparation thereof and the uses thereof.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The examples which follow illustrate the present application.

The invention will be understood more clearly if reference is made to the appended drawings wherein.

DETAILED DESCRIPTION OF THE INVENTION

Example 1: Preparation of a Sol Gel Matrix

In 11.74 mL of methanol stirred and cooled to approximately −25° C., 300 µL of 0.1 M AAP is added. 10.74 mL of tetramethyl-orthosilicate is then added, followed by 0.528 mL of aminopropyl-triethoxysilane. 300 µL of 0.1 M potassium hexacyanoferrate and 6.396 mL of 0.05 M borate buffer solution at pH 9 are then added.

The sol is removed to pour it into moulds which are sealed hermetically for 48 hours, and the solvents are progressively evaporated in a nitrogen atmosphere.

Example 1A: Preparation of a Sol Gel Matrix (with Another Formulation)

In 6.926 mL methanol stirred and cooled to approximately −25° C., 300 µL of 0.1 M AAP is added. 6.447 mL of tetramethyl-orthosilicate is then added, followed by 0.252 mL of (3-chloropropyl)trimethoxysilane. 300 µL of 0.1 M potassium hexacyanoferrate, 9.776 mL of $H_2O$ and 6.0 mL of 0.05 M borate buffer solution at pH 9 are the added.

The sol is removed to pour it into moulds which are sealed hermetically for 48 hours, and the solvents are progressively evaporated in a nitrogen atmosphere.

For the matrices of Examples 1 and 1A, various shapes were obtained according to the mould used. The following moulds were used:
a. Parallelepipedic moulds having the dimensions 2*10*20, in mm.
b. Parallelepipedic moulds having the dimensions 4*10*50 in mm.

They were filled with a volume of approximately 400 µL for type a moulds and 1 mL for type b moulds.

The materials according to the invention obtained are sol gel matrices. They are transparent and free from cracks. Protected from light, they can be stored for several months.

Figure 1:
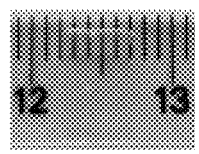
FIG. 1 represents a top view photograph of a block of material from example 1 placed on a ruler.

FIG. 1 is a photograph of a material according to the invention placed on a ruler. The matrix measures in this case approximately 5 mm wide by 8.2 millimeters long. The thickness thereof is approximately 1 millimeter.

Experiment 1: Exposure of a Matrix to a Gas Stream Containing Phenol

The function of the materials according to the invention is based on a chemical reaction taking place in the matrix which generates an optically detectable signal. Tracking this optical signal over time makes it possible to determine the reaction rate, which can then be correlated with the concentration of gaseous compound under test by means of a calibration curve. The optical detection is rapid and feasible in situ in a single step.

A Sol-Gel matrix, according to example 1 or example 1A, prepared using a type a mould is exposed to a continuous gas stream of 500 mL/min containing a fixed concentration of 100 ppb of phenol in 50% relative humidity. The gaseous phenol is generated using a permeation oven, and then diluted with air to the concentration sought, and conveyed to the input of a measurement cell housing the Sol-Gel matrix using a tube approximately 3 mm in diameter, and having a gas input and output suitable for such tubes, along with an optical input and output for connecting the optical fibres. To limit interfering light, the cell is embodied in such a way that the ambient light does not enter the cell.

During exposure, the pollutant circulates in the cell while a deuterium-halogen source (Ocean Optics, DH-2000-BAL) illuminates the matrix via the optical input and absorption spectra are recorded by a UV-Visible spectrophotometer (Ocean Optics, QE65000). Tracking of the variation of the absorbance over the exposure time makes it possible to observe the appearance of a characteristic peak at 510 nm of the reaction product between phenol and the reagent capable of generating a stained product by forming a bond with phenol incorporated in the material according to the invention.

Figure 2:
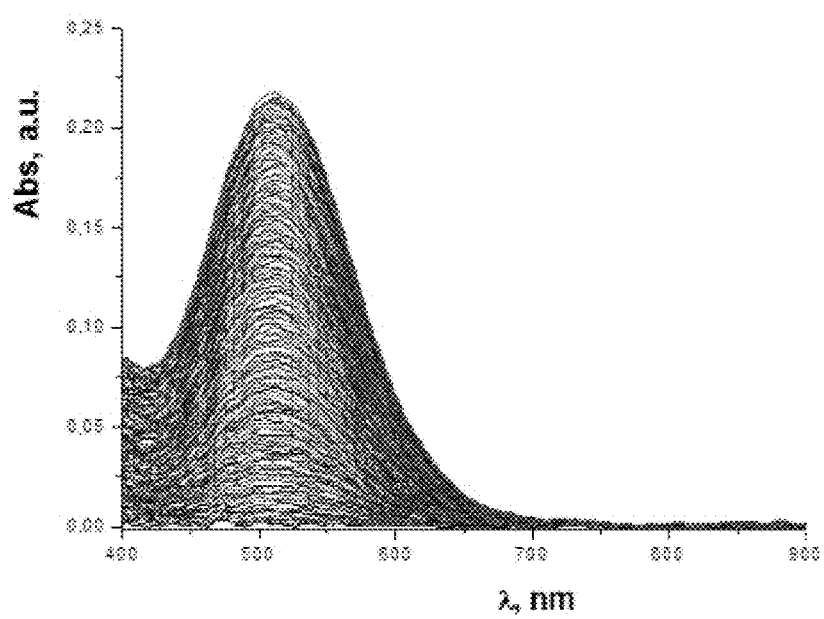
FIG. 2 represents the progression of the absorption spectra of experiment 1 for a matrix of example 1.
Figure 2A:
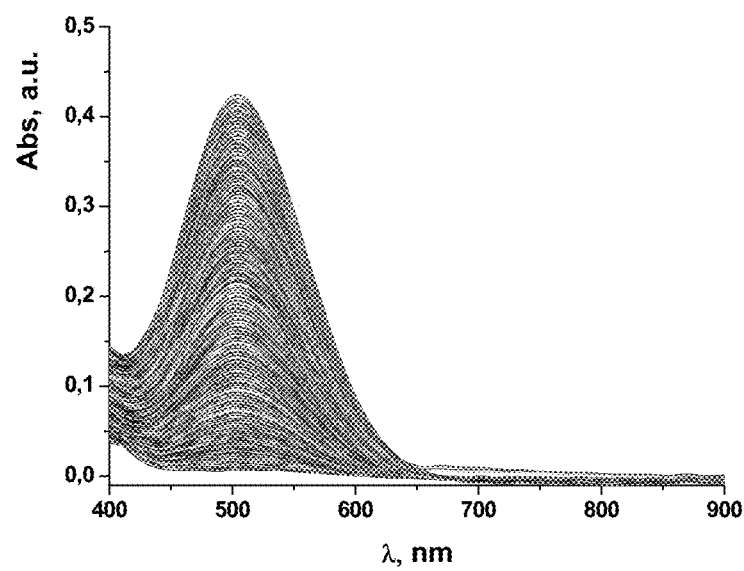
FIG. 2A represents the progression of the absorption spectra of experiment 1 for a matrix of example 1A.
Figure 3:
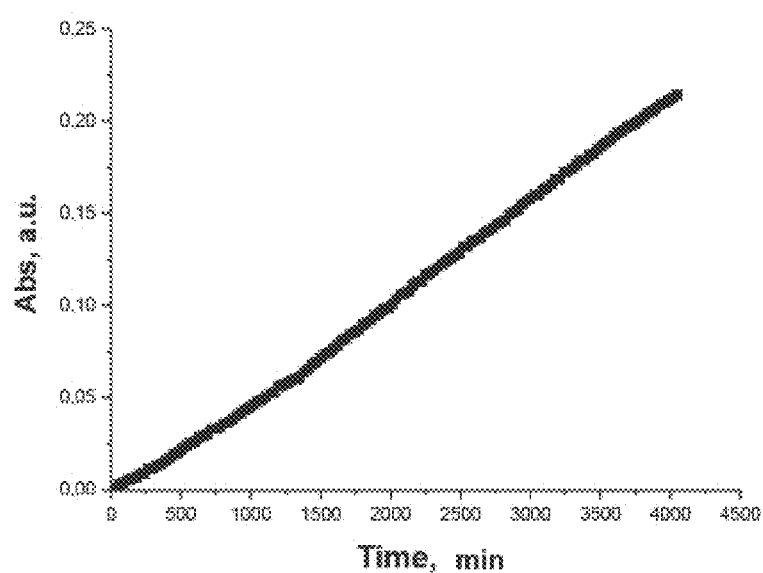
FIG. 3 represents the progression of the absorbance over time at 510 nm in experiment 1 for a matrix of example 1.
Figure 3A:
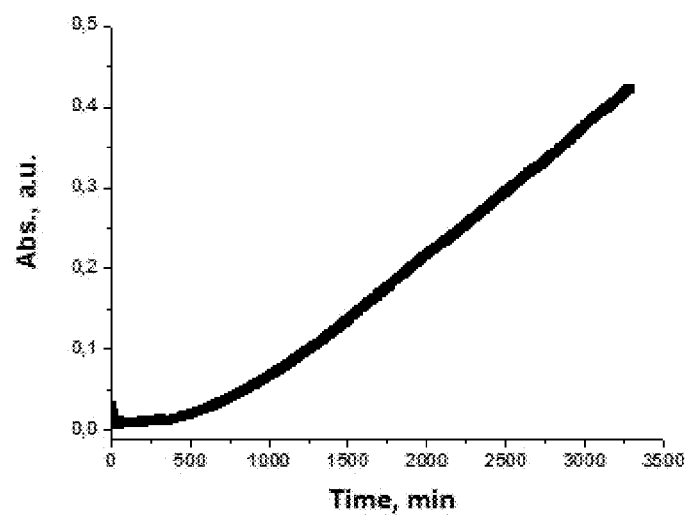
FIG. 3A represents the progression of the absorbance over time at 510 nm in experiment 1 for a matrix of example 1A
Figure 4:
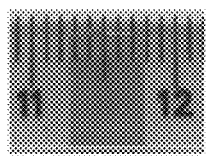
FIG. 4 represents a photograph of a block of material from example 1 after exposure to phenol.

The intensity of this peak increases in the course of the exposure. The spectra are recorded in FIG. 2 for the matrix of example 1 and in FIG. 2A for the matrix of example 1A and the progression of the absorbance over time at 510 nm in FIG. 3 for the matrix of example 1 and in FIG. 3A for the matrix of example 1A. The photo of a matrix after exposure is shown in FIG. 4.

The progression of the spectra (FIGS. 2 and 2A) demonstrates that the absorbance of the material increases in the presence of phenol. The slope at 510 nm (FIGS. 3 and 3A) shows that the increase in absorbance can be correlated at a given wavelength with the interaction of a certain concentration of phenol with the material. The comparison of the photo in FIG. 4 and the photo in FIG. 1 shows that the increase in absorbance is visible to the naked eye.

Experiment 2: Calibration Curve of Phenol

Figure 5:
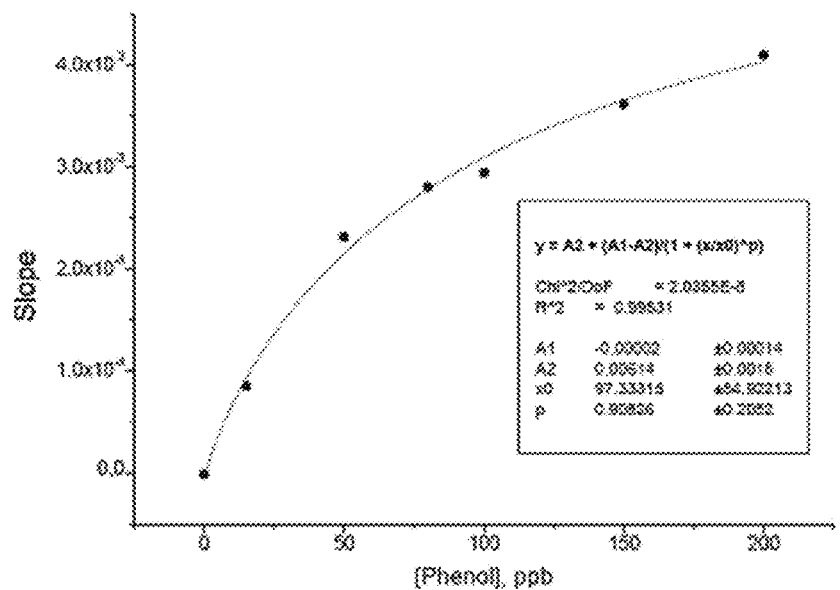
FIG. 5 represents a calibration curve for the detection/assay of phenol.

The same method as in experiment 3 is repeated for different phenol concentrations at a flow rate of 500 mL/min. The rate of formation of the reaction product between phenol and the matrix doped with probe molecules is dependent on the phenol concentration contained in the gas stream. As such, plotting the value of the slopes as a function of the concentration gives the calibration curve for phenol detection; such a calibration curve is represented in FIG. 5. The results obtained demonstrate that it is possible to measure the concentration of phenol in a gas mixture using a sol gel matrix according to the invention.

Experiment 3: Application of the Method to Other Phenol Derivatives

The procedure as described in experiment 1 was followed, but using various phenol derivatives, i.e. 4-methoxyphenol, 2-nitrophenol, 2,4-dichlorophenol, and naphthol. The results obtained are shown in FIG. 6.

The phenol derivatives can also be detected equally well, but the maximum absorption wavelength differs slightly from that observed for phenol.

Figure 6:
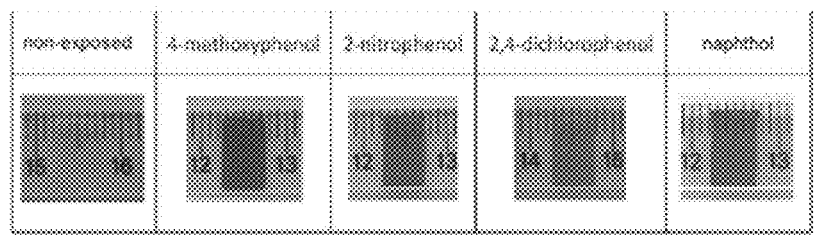
FIG. 6 represents photographs of blocks of material from example 1 after exposure to various phenol derivatives.

Consequently, the colour of the matrix after exposure is also different, as shown by the comparison of FIG. 1 and FIG. 6. As such, the detection can be qualitative (which is possible with the naked eye) or quantitative (by making a measurement by absorbance or reflectance for example).

Figure 7:
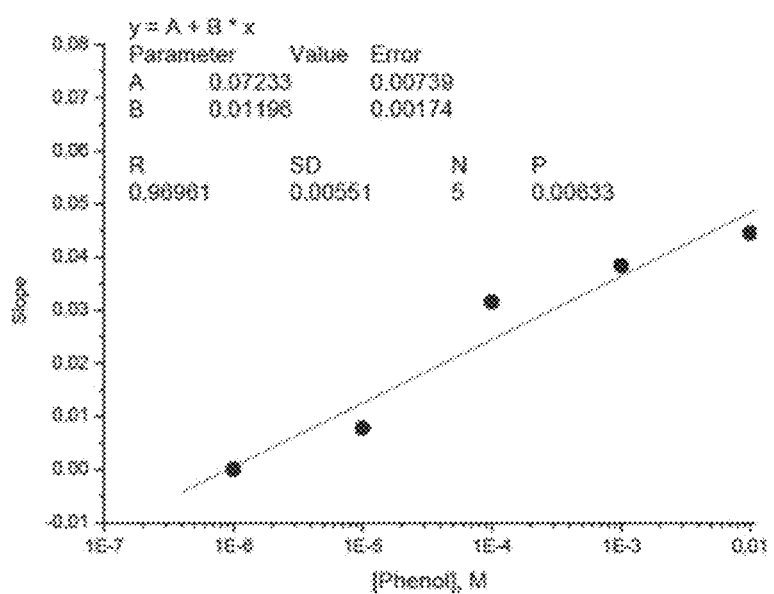
FIG. 7 represents a calibration curve for the detection of phenol, in aqueous solution.

Experiment 4: Calibration of Detection of Phenol in Aqueous Solution with a Sol-Gel Matrix A Sol-Gel matrix according to example 1 was placed in an aqueous phenol solution at a known concentration. The progression of the absorbance of the solution over time was monitored at 506 nm using a UV-Vis spectrophotometer. This method was repeated for different phenol concentrations. The rate of reaction between the probe molecules of the matrix and phenol is dependent on the phenol concentration. The plot of the value of the slopes as a function of the concentration constitutes the calibration curve for the detection of phenol; the result obtained is represented in FIG. 7. The results obtained demonstrate that it is possible to measure the concentration of phenol in an aqueous solution using a sol gel matrix according to the invention.

Comparative Experiment:

When phenol is added last for the reaction in aqueous solution, in the presence of a significant excess of potassium hexacyanoferrate, the change of colour does not OMIT.

Even slightly below the typical ratio described in the literature, i.e. with a ratio of [AAP]:[potassium hexacyanoferrate]=1:5, the change of colour is not significant.

The change of colour with the addition of phenol last becomes significant only by modifying the ratio used in the reference method. The reaction works properly when phenol is added last if the different constituents are used under the conditions indicated above in the description. Notably the use either of a slight excess of oxidant compounds such as potassium hexacyanoferrate, an excess of reagent capable of generating a stained product by forming a bond with phenol, or an equivalent quantity of reagent capable of generating a stained product by forming a bond with phenol and oxidant compounds and the relationship between these ratios and the possibility of adding phenol as the final reagent, had never been envisaged.

As such in conclusion, the colorimetric method according to the present invention provides a certain number of innovations including the addition of phenol last (essential for performing detection using a matrix incorporating all the reagents in advance), the incorporation of basic components, the incorporation of an oxidant in the same matrix which can be stored for over 6 months, and in some cases an original ratio of [stained reagent]/[oxidant].

The invention claimed is:
1. A monolithic nanoporous material, which is self-standing (i.e. self-supported or cohesive), solid and transparent, essentially devoid of cracks, transparent to UV radiation, and obtained by the Sol-Gel process, said material having a basic nature and comprising:
   a reagent capable of generating a stained product by forming a bond with phenol or a phenol derivative,
   a basic compound or mixture of basic compounds, and
   an oxidant compound or mixture of oxidant compounds,
   wherein the ratio by weight of the reagent capable of generating a stained product by forming a bond with phenol or a phenol derivative: the oxidant compound or mixture of oxidant compounds is 15:1 to 1:3.

2. The monolithic nanoporous material according to claim 1, wherein the reagent capable of generating a stained product is 4-aminoantipyrine (AAP) or a derivative of AAP having formula I

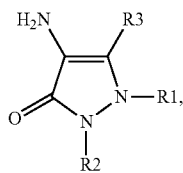

formula I wherein:
R1 is an alkyl radical containing 1 to 30 carbon atoms, linear or branched, or an aryl radical;
R2 is a phenyl or para-aminophenyl radical; and
R3 is an alkyl radical containing 1 to 30 carbon atoms, linear or branched.

3. The monolithic nanoporous material according to claim 1, wherein the oxidant compound or oxidant compounds are chosen in the group consisting of potassium persulphate, potassium peroxomonosulphate, hydrogen peroxide and potassium hexacyanoferrate.

4. The monolithic nanoporous material according to claim 1, wherein the basic compound or mixture of basic compounds are chosen in the group consisting of a borate, phosphate, 2-amino-2-(hydroxymethyl)-1,3-propanediol, carbonate, glycine-sodium hydroxide, or sodium hydroxide buffer.

5. The monolithic nanoporous material according to claim 1, wherein
the reagent capable of generating a stained product by forming a bond with phenol or a phenol derivative is AAP,
the basic compound or mixture of basic compounds is chosen among borate ions and sodium hydroxide, and
the oxidant compound or oxidant compounds are selected from the group consisting of potassium hexacyanoferrate, potassium persulphate, potassium peroxomonosulphate, hydrogen peroxide, and a mixture of potassium hexacyanoferrate and one or a plurality of further oxidant compounds.

6. The monolithic nanoporous material according to claim 1, containing by weight
25% to 0.005% of probe molecule,
5% to 0.05% of basic compound or mixture of basic compounds, and
15% to 0.01% of oxidant compound or mixture of oxidant compounds.

7. The monolithic nanoporous material according to claim 1, containing by weight
50% to 0.05% of probe molecule,
5% to 0.05% of basic compound or mixture of basic compounds, and
25% to 0.01% of oxidant compound or mixture of oxidant compounds.

8. The monolithic nanoporous material according to claim 1, wherein the reagent capable of generating a stained product is 4-aminoantipyrine (AAP) or a derivative of AAP having formula I

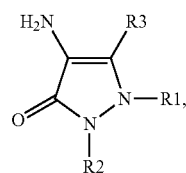

formula I wherein:
R1 is an alkyl radical containing 1 to 30 carbon atoms, linear or branched, or an aryl radical;
R2 is a phenyl or para-aminophenyl radical; and
R3 is a substituted phenyl of an alkyl radical containing 1 to 30 carbon atoms, linear or branched.

9. The monolithic nanoporous material according to claim 1, wherein the ratio by weight of the reagent capable of generating a stained product by forming a bond with phenol or a phenol derivative: the oxidant compound or mixture of oxidant compounds is 10:1 to 1:3.

10. A monolithic nanoporous material according to claim 1, wherein the ratio by weight of the reagent capable of generating a stained product by forming a bond with phenol or a phenol derivative: the oxidant compound or mixture of oxidant compounds is 5:1 to 1:2.

* * * * *